(12) United States Patent
Iniewski et al.

(10) Patent No.: US 10,396,109 B2
(45) Date of Patent: Aug. 27, 2019

(54) LOCAL STORAGE DEVICE IN HIGH FLUX SEMICONDUCTOR RADIATION DETECTORS AND METHODS OF OPERATING THEREOF

(71) Applicant: REDLEN TECHNOLOGIES, Saanichton (CA)

(72) Inventors: Kris Iniewski, Coquitlam (CA); Glenn Bindley, Vancouver (CA); Robert Crestani, Vancouver (CA)

(73) Assignee: Redlen Technologies, Inc., Saanichton (CA)

( * ) Notice: Subject to any disclaimer, the term of this patent is extended or adjusted under 35 U.S.C. 154(b) by 372 days.

(21) Appl. No.: 15/095,786

(22) Filed: Apr. 11, 2016

(65) Prior Publication Data

US 2017/0290555 A1 Oct. 12, 2017

(51) Int. Cl.
*A61B 6/00* (2006.01)
*A61B 6/03* (2006.01)
(Continued)

(52) U.S. Cl.
CPC ........ *H01L 27/14609* (2013.01); *A61B 6/482* (2013.01); *G01T 1/1663* (2013.01);
(Continued)

(58) Field of Classification Search
CPC ........... A61B 6/00; A61B 6/42; A61B 6/4208; A61B 6/4233; A61B 6/4241; A61B 6/48; A61B 6/82; A61B 6/52; A61B 6/5205; A61B 6/5294; A61B 6/54; A61B 6/56; A61B 6/563; H04N 5/30; H04N 5/32; H04N 5/335; H04N 5/38; A61N 1/025;
(Continued)

(56) References Cited

U.S. PATENT DOCUMENTS

| | | | | |
|---|---|---|---|---|
| 5,604,608 A | * | 2/1997 | Walsh | ................. H04N 1/0402 358/468 |
| 6,362,482 B1 | * | 3/2002 | Stettner | ................. G01T 1/1644 250/370.01 |

(Continued)

OTHER PUBLICATIONS

Kalender, W.A., "*Trends in X-Ray CT Imaging and Respective Demands on Detectors*," Institute of Medical Physics, iworld 2008, Helsinki, 33 pages, (2008).

(Continued)

*Primary Examiner* — Anastasia Midkiff
(74) *Attorney, Agent, or Firm* — The Marbury Law Group, PLLC

(57) ABSTRACT

A detector element circuit for a CT imaging system may include a plurality of sensors for detecting photons passing through an object and a first electronic component configured to determine an energy of photons detected by the plurality of sensors and generate photon count data, which may be a count of detected photons in one or more energy bins. The detector element circuit may further include a second electronic component configured to receive the photon count data from the first electronic component and is clocked at a first clock rate; a local memory storage configured to receive the photon count data from the second electronic component at the first clock rate and to output the photon count data at a second clock rate.

16 Claims, 4 Drawing Sheets

(51) Int. Cl.

| | | |
|---|---|---|
| *G01T 1/24* | (2006.01) | |
| *G01T 1/29* | (2006.01) | |
| *G06T 1/60* | (2006.01) | |
| *G01T 1/166* | (2006.01) | |
| *H03K 23/40* | (2006.01) | |
| *H03K 5/135* | (2006.01) | |
| *H01L 27/146* | (2006.01) | |
| *H03K 19/177* | (2006.01) | |

(52) U.S. Cl.
CPC .............. *G01T 1/246* (2013.01); *G01T 1/247* (2013.01); *G06T 1/60* (2013.01); *H03K 5/135* (2013.01); *H03K 19/17716* (2013.01); *H03K 23/40* (2013.01); *A61B 6/032* (2013.01); *A61B 6/4233* (2013.01); *G01N 2223/304* (2013.01); *G01N 2223/401* (2013.01); *G01T 1/2985* (2013.01); *G06T 2207/10081* (2013.01); *H01L 27/14676* (2013.01); *H01L 2225/06513* (2013.01)

(58) Field of Classification Search
CPC ............ H05G 1/00; H05G 1/08; G16H 10/00; G16H 30/00; G16H 40/60; G16H 40/63; G01T 1/00; G01T 1/16; G01T 1/1663; G01T 1/24; G01T 1/244–1/247; G01T 7/00; H03K 5/00; H03K 5/00104; H03K 5/05; H03K 5/13; H03K 5/135; H03K 19/01728; H03K 19/17716; H03K 23/002; H03K 23/40; G01N 23/00; G01N 23/02; G01N 23/06; G01N 23/083; G01N 23/087; G01N 2223/30; G01N 2223/304; G01N 2223/40; G01N 2223/401; G01N 2223/413; G01N 2223/423; G01N 2223/50; G01N 2223/501; H01L 27/00; H01L 27/14; H01L 27/144; H01L 27/1446; H01L 27/14601; H01L 27/14609; H01L 27/14658; H01L 27/14676; H01L 27/148; H01L 27/14806; H01L 27/14837; H01L 2225/00; H01L 2225/03; H01L 2225/04; H01L 2225/065; H01L 2225/06503; H01L 2225/06513; G06T 1/00; G06T 1/0007; G06T 1/20; G06T 1/60; G06T 2200/00; G06T 2200/28; G06T 2207/00; G06T 2207/10; G06T 2207/10072; G06T 2207/10081; G06T 2207/10116; G06T 2207/20; G06T 2210/41; G06T 2211/00; G06T 2211/40; G06T 2211/408

See application file for complete search history.

(56) References Cited

U.S. PATENT DOCUMENTS

| | | | |
|---|---|---|---|
| 6,597,630 B1* | 7/2003 | Kubo | G11C 7/1051 365/189.05 |
| 2002/0037068 A1 | 3/2002 | Oikawa | |
| 2007/0121781 A1 | 5/2007 | Meirav et al. | |
| 2008/0165921 A1 | 7/2008 | Tkaczyk et al. | |
| 2010/0098210 A1 | 4/2010 | Hackenschmied et al. | |
| 2010/0213353 A1* | 8/2010 | Dierickx | G01T 1/17 250/214 R |
| 2014/0183371 A1* | 7/2014 | Roessl | G01T 1/241 250/370.09 |
| 2015/0234059 A1 | 8/2015 | Roessl et al. | |

OTHER PUBLICATIONS

Hu, H. et al., "Four Multidetector-Row Helical CT: Image Quality and Volume Coverage Speed," Radiology, vol. 215, No. 1, pp. 55-62, (2000).

Chmeissani, M. et al, "First Experimental Tests with a CdTe Photon Counting Pixel Detector Hybridized with a Medipix2 Readout Chip," IEEE Transactions on Nuclear Science, vol. 51, No. 5, pp. 2379-2385, (2004).

Shikhaliev, PM. et al, "Tilted Angle CZT Detector for Photon Counting/Energy Weighting X-ray and CT Imaging," Phys Med Biol., vol. 51, No. 17, pp. 4267-4287, (2006).

Iniewski, K. et al, "CZT Growth, Characterization, Fabrication, and Electronics for Operation at >100 Mcps/mm$^2$," Workshop on Medical Applications of Spectroscopic X-Ray Detectors, CERN, 1 page, (2015).

Murphy, D.T. et al., "Technical Advancements in Dual Energy," Published in P.M. Carrascosa et al. (eds.), Dual-Energy CT in Cardiovascular Imaging, Springer International Publishing, Switzerland, pp. 151-152, (2015).

Taguchi, K. et al, "An Analytical Model of the Effects of Pulse Pileup on the Energy Spectrum Recorded by Energy Resolved Photon Counting X-ray Detectors," Medical Physics, vol. 37, No. 8, pp. 3957-3969, (2010).

U.S. Appl. No. 15/014,707, filed Feb. 3, 2016, El-Hanany et al.

* cited by examiner

LOCAL STORAGE DEVICE IN HIGH FLUX SEMICONDUCTOR RADIATION DETECTORS AND METHODS OF OPERATING THEREOF

FIELD

The present application is directed to the field of radiation detectors, and specifically to systems and methods for collecting, storing, and outputting data from a radiation detector.

BACKGROUND

In computed tomography (CT) imaging systems, an X-ray source emits a fan-shaped beam toward an object, such as piece of baggage at an airport scanner or patient in a medical diagnostic clinic, or any other biological or non-biological object that is being imaged. The X-ray beam is attenuated by the object and subsequently detected by a detector element, such as a Cadmium Zinc Telluride (CdZnTe, or CZT) detector. Other direct conversion detectors such as Cadmium Telluride (CdTe), Gallium Arsenide (GaAs), or Silicon (Si), or any indirect director based on scintillator material may also be used in CT imaging systems. Image slices collected by scanning the object may, when joined together, produce 3-dimensional cross-section images of the object.

In typical CT imaging systems, a detector array that includes a number of detector elements may each produce a dedicated electrical signal that indicates the level of attenuation received by each detector element. The electrical signals may be transmitted to a data processing card for analysis. Finally, using image reconstruction techniques an image is produced. The intensity of the attenuated beam received by each detector element is dependent upon the attenuation of the X-ray beam by the object. For example, when scanning a human body, bone turns up white, air turns up black, and tissues and mucous turn up in shades of gray. When no object is present in the CT scanner the detected intensity, or count rate, could reach values as high as $10^9$ counts per second per millimeter squared (cps/mm$^2$). On the other hand, if the scanned object is thick the count rate could be orders of magnitude lower. Thus the detected count rate could vary significantly during the X-ray tube rotation process while the image is being acquired.

SUMMARY

Various systems and methods described herein provide a way to control the data output rate of a CT imaging system separately from the data collection and processing rate of the radiation detectors. Various apparatuses described herein may include a detector element circuit for a CT imaging system that includes a plurality of radiation sensors for detecting photons attenuated by an object and a first electronic component (e.g., an ASIC-Application Specific Integrated Circuits) configured to determine an energy of photons detected by the plurality of radiation sensors and generate photon count data. The photon count data may be a count of detected photons in one or more energy bins. The detector element circuit may further include a second electronic component (e.g., a FPGA-Field Programmable Gate Array) configured to receive the photon count data from the first electronic component, and a local memory storage configured to receive the photon count data from the second electronic component at the first clock rate and to output the photon count data. The second electronic component may be clocked at a first clock rate. The local memory storage may buffer and then output the photon count data to an input/output interface at a second, different clock rate.

Various systems described herein may include a CT imaging system that includes a gantry comprising a radiation source and a detector array. The detector array may detect radiation emitted from the radiation source and attenuated by an object located in the gantry, and may include a plurality of detector element circuits that each includes a plurality of radiation sensors and a local memory storage for buffering data generated by the radiation sensors. The CT imaging system may further include a computer located remotely from the gantry that receives data buffered by the local memory storage of each detector element circuit. Each detector element circuit may transmit the buffered data to a computer over a wired or wireless connection. The local memory storage in each of the plurality of detector element circuits may be clocked at a separate clock rate than other components in the detector element circuit.

Various methods described herein may include a method of operating a CT imaging system that includes detecting photons emitted by an X-ray source and attenuated by an object, generating photon count data by counting a number of detected photons in a plurality of energy bins, buffering the photon count data at a first clock rate, and outputting the photon count data at a second clock rate. A detector array in the CT imaging system may detect the photons, and the detector array may include a plurality of detector element circuit, each one of which may include a plurality of radiation sensors. Each detector element circuit may also include a local memory storage for buffering the photon count data. The local memory storage may be clocked at the second clock rate, while an electronic component in each detector circuit may transfer the photon count data to the local memory storage at the first clock rate. The photon count data may be outputted to an external computer.

DETAILED DESCRIPTION

Figure 1:
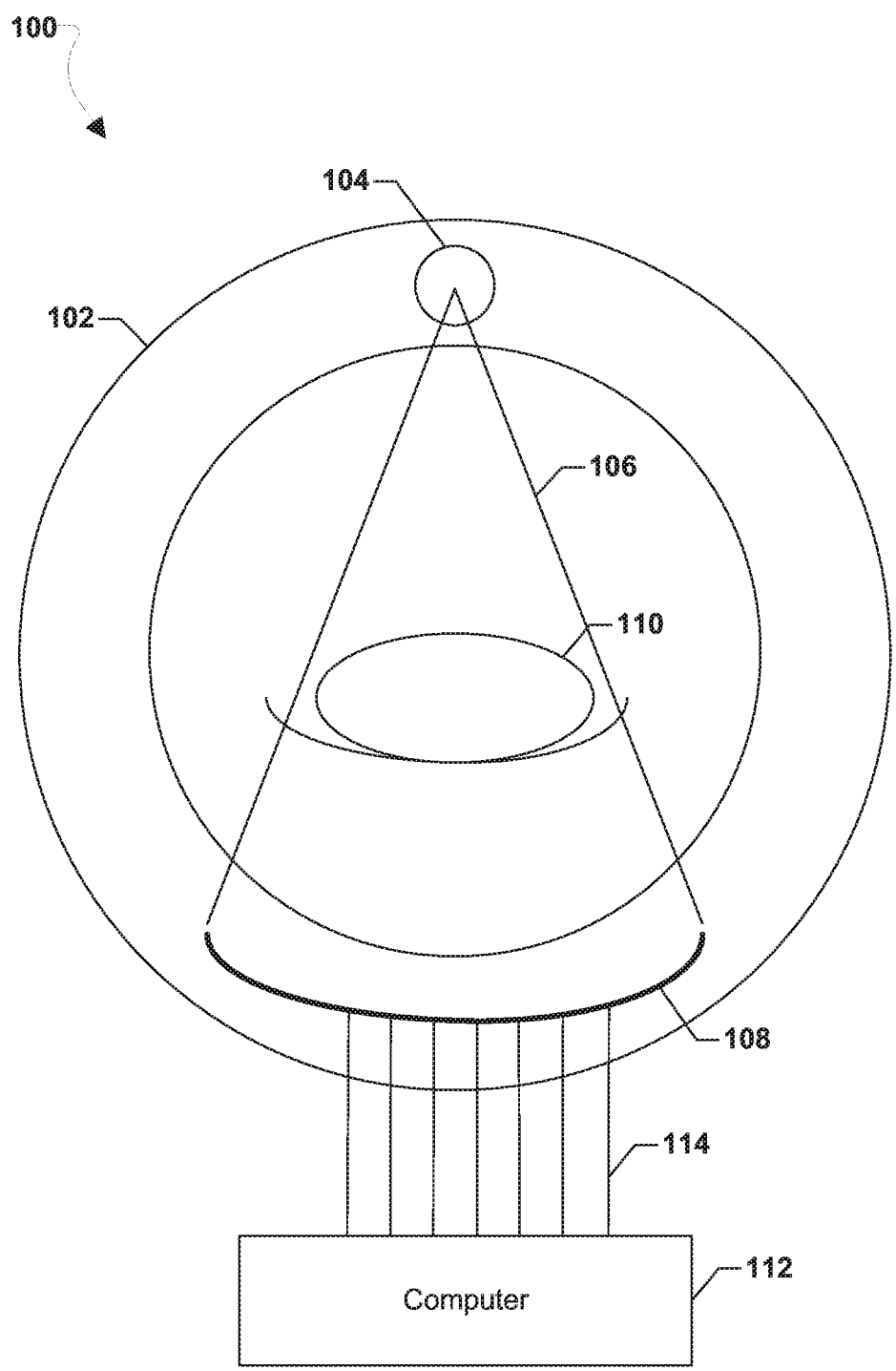
FIG. 1 is a functional block diagram of a CT imaging system according to various embodiments.

As imaging technology advances, CT imaging systems may be capable of generating large amounts of imaging data. For example, some CT imaging systems may utilize pixel sizes of 1 mm and have one voltage threshold (or energy bin) in analog to digital (A/D) signal processing. Other, newer CT imaging systems may utilize pixel sizes of 0.5 mm or smaller (which increases spatial resolution) and have multiple energy bins, such as four (which increases object discrimination), potentially leading to an increase of transmitted data by a factor of 16 or more over CT imaging systems with larger pixels and only one energy bin. The amount of data that is generated and transferred from a single detector element of the detector array may also increase by the same factor (e.g., 1 gigabyte (Gb) versus 16 Gb), but has to be transferred within the same timeframe, which could be on the order of fractions of a second. Accommodating such increases in data generation and transmission could increase the cost of CT imaging systems, or else could lead to performance issues in CT imaging systems, such as bottlenecks or slowdowns caused by data that exceeds bandwidth limitations of the CT imaging hardware. This issue may become progressively worse as pixel sizes continue to decrease and the number of energy bins used to sort the detected photons increases.

The various apparatuses, systems and methods disclosed herein may provide a way to digitize, store, and transfer large amounts of data generated by CT imaging systems utilizing small pixels and/or more energy bins. A CT imaging system may include a detector array with a number of detector elements, each detector element including a number of photon counting detectors as pixels. Each detector element may include an electronic component such as an ASIC for digitizing, storing, and transferring the photons detected by the detector element. After digitizing the sensor data from the pixels, the detector element circuit may include a field programmable gate array (FPGA) or other electronic component that receives the digitized data. The data may then be transferred to a local memory storage, which buffers and outputs the data off the scanner to a remote processing and imaging system.

The FPGA and the local memory storage may be clocked at different clock rates so that the rate of data output from the FPGA and the local memory storage may be adjusted relative to each other. For example, the local memory storage may receive photon count data from the FPGA at a first clock rate, and may output the data according to a second clock rate. The second clock rate may be slower than the first clock rate. This allows the local memory storage to temporarily buffer the detector element data, and then transfer the data at rates that may be handled by the rest of the CT imaging system. For example, the local memory storage may output data at certain rates that do not exceed the maximum bandwidth of the wired or wireless transmission medium to a remote processing and imaging system, or that does not exceed the data processing speed of an imaging application that processes the data. This may result in a transfer rate that is "near real time" but sufficient for practical imaging applications.

FIG. 1 is a functional block diagram of a CT imaging system 100 according to various embodiments. The CT imaging system 100 may include a gantry 102, which may include a moving part, such as a circular, rotating frame with an X-ray source 104 mounted on one side and a curved detector array 108 mounted on the other side. The gantry 102 may also include a stationary (i.e., non-moving) part, such as a support, legs, mounting frame, etc., which rests on the floor and supports the moving part. The X-ray source 104 may emit a fan-shaped X-ray beam 106 as the gantry 102 and the X-ray source 104 rotates around an object 110 inside the CT imaging system 100. The object 110 may be any biological (e.g., human patient) or non-biological sample to be scanned. After the X-ray beam 106 is attenuated by the object 110, the X-ray beam 106 is received by the detector array 108. The curved shape of the detector array 108 allows the CT imaging system 100 to create a 360° continuous circular ring of the image of the object 110 by rotating the gantry 102 around the object 110.

For each complete rotation of the gantry 102, one cross-sectional element of the object 110 is acquired. As the gantry 102 continues to rotate, the detector array 108 takes numerous snapshots called "profiles." Typically, about 1,000 profiles are taken in one rotation of the gantry 102. The object 110 may slowly pass through the rotating gantry 102 so that the detector array 108 captures incremental cross-sectional profiles of the entire object 110. Alternatively, the object 110 may remain stationary and the gantry 102 is moved along the length of the object 110 as the gantry 102 is rotated. The data generated by the detector array 108 is passed to a computer 112 that is located remotely from the gantry 102 via a connection 114. The connection 114 may be any type of wired or wireless connection. If connection 114 is a wired connection, then it include a slip ring electrical connection between the rotating part of the gantry 102 supporting the detector 108 and a stationary support part of the gantry which supports the rotating part (e.g., the rotating ring). If the connection 114 comprises a wireless connection, then the detector 108 mounted on the rotating part of the gantry 102 may contain any suitable wireless transceiver to communicate data with another wireless transceiver that is not located on the rotating part of the gantry and which is in communication with the computer 112. The computer 112 may include processing and imaging applications that analyze each profile obtained by the detector array 108, and the full set of profiles from each rotation is compiled to form a two-dimensional image of a cross-sectional element of the object 110.

The design of the CT imaging system 100 as contemplated in the various embodiments is not limited to the architecture as illustrated in FIG. 1. CT imaging systems may be designed in various architectures and configurations. For example, a CT imaging system may have a helical architecture. In a helical CT imaging scanner, the X-ray source and detector array are attached to a freely rotating gantry. During a scan, a table moves the object smoothly through the scanner creating helical path traced out by the X-ray beam. Slip rings enable the transfer of power and data on and off the rotating gantry. A switched mode power supply may be used to power the X-ray source while at the same time still be small enough to be installed on the gantry.

In other embodiments, the CT imaging system may be a tomosynthesis CT imaging system. In a tomosynthesis CT scanner, the gantry may move in a limited rotation angle (e.g., between 15-60 degrees) in order to detect a cross-sectional slice of the object. The tomosynthesis CT scanner may be able to acquire slices at different depths and with different thicknesses that may be constructed via image processing.

Figure 2:
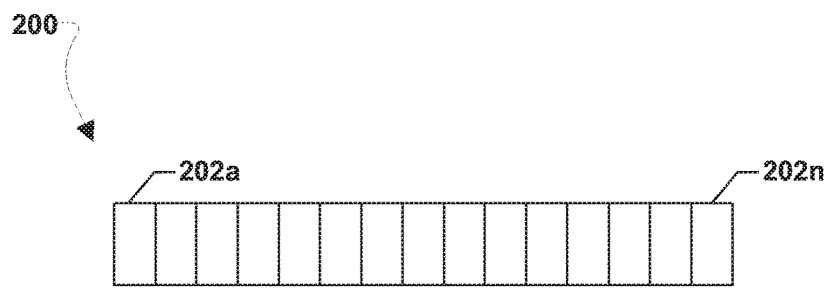
FIG. 2 is a block diagram of a detector array according to various embodiments.

FIG. 2 illustrates a detector array 200 for use in CT imaging systems according to various embodiments. The detector array 200 may be a single slice detector array or a multi-slice detector array. For example, a single slice configuration the detector array 200 is one dimensional and includes a large number (typically 100 or more) of detector elements 202a-202n, or data elements, in a single row across the detector array 200 to intercept the X-ray beam. The detector elements 202a-202n, which may be photon sensors, are monolithic in the slice thickness direction. In other words, each detector element 202a-202n is an individual detector element that is long enough to capture the entire X-ray beam width.

In a multi-slice configuration, in the detector array 200, the detector elements 202a-202n are not individual monolithic detectors but rather composed of a number of smaller detector elements, forming a 2-dimensional array. Rather than a single row of detector elements intercepting the X-ray beam, there are now multiple, parallel rows of detector elements (e.g., 32, 64, 128, or 256 rows). For example, each detector element 202a-202n may have several thousand pixel sensors of size 0.5 mm or smaller, arranged in an array. Various detector array or CT imaging system manufacturers may use a different number of detector elements 202a-202n in the detector array 200, of possibly different slice thickness (e.g., 32 or 64). Detector elements that may be used in the detector array and methods for fabricating such detector elements are described in U.S. patent application Ser. No. 15/014,707, filed Feb. 3, 2016 and entitled "High Performance Radiation Detectors and Methods of Fabricating Thereof," which is hereby incorporated by reference in its entirety.

Utilizing multi-slice detector array architecture may generate more images as compared to a single slice architecture. For example, covering a 40 cm scan range with contiguous single slice 5 mm detector elements (whether acquired axially or helically) would generate 80 images. Multi-slice scanning of the same range with a collimation of 4×1.25 mm to produce both 1.25 and 5 mm detector elements would generate 400 images: 320 images with a thickness of 1.25 mm and 80 images with a thickness of 5 mm, resulting in a fivefold increase in number of images compared to the single slice architecture. As the number of detector elements increase (e.g., 16, 32, 64, 128 or 256 elements) the number of images also increases. The multi-slice detector array architectures may utilize a picture archiving and communication system (PACS) to transfer, process, and interpret this large amount of data.

In addition to increasing the number of detector elements and reducing the size of each pixel in the image, using photon counting detectors may also increase the amount of data generated by a CT imaging system. Photon counting CT detectors may be manufactured from a number of semiconductor materials, including CdTe, CZT, Selenium, and Silicon. Photon counting detectors have may be utilized to reduce noise and enhance contrast compared to other types of detectors.

Photon counting detectors may set an energy or voltage threshold above a noise floor, thereby eliminating background electronic noise. Although the variation in the detected energy of each photon affects the energy resolution, it does not affect the number of photons counted, thus eliminating Swank noise. Furthermore, photon counting detectors have the potential to reduce the overlap in the spectra of the high and low energy detected photons compared to dual kVp or dual-layer systems since good energy resolution can be achieved and maintained at high flux conditions.

Photon counting detectors may also set additional energy/voltage thresholds to sort detected photons into energy bins based on the energy of each photon or the voltage generated by the received photon. The number of energy bins may range from two to six. For example, a photon counting detector may have four energy bins: 20-40 kilo-electron-volts (keV), 40-60 keV, 60-80 keV, and 80-100 keV. The larger number of energy bins, the better the material discrimination, which may aid in medical diagnosis or other applications. Each additional threshold or energy bin may generate additional data that is transferred and processed by the CT imaging system. A combination of fast photon counting detectors and application specific integrated circuits (ASICs) which read out the signals from the detectors may increase the output count rate (OCR) of the CT imaging system. For example, CdTe and CZT based photon counting detectors have been used to create full field of view (FOV) clinical CT imaging systems.

Thus a CT imaging system with a large number of detector elements (e.g., 100), small pixel sizes (e.g., 2000 per slice), and photon counting detectors with multiple energy bins may result in a large amount of data is generated and transferred from each detector element to a computing element, like an end-user computer or server. Current CT imaging systems may not be able to process the data efficiently, leading to bottlenecks in the system.

The various embodiments disclosed herein provide a way to control the transfer of data from the detector array to an external computer through the use of an intermediate memory storage component located on each detector element of the detector array. This local memory storage component may buffer the photon count data and may be clocked at a different clock rate than the other components in the detector element circuit to control the rate at which data is outputted from the detector element.

Figure 3:
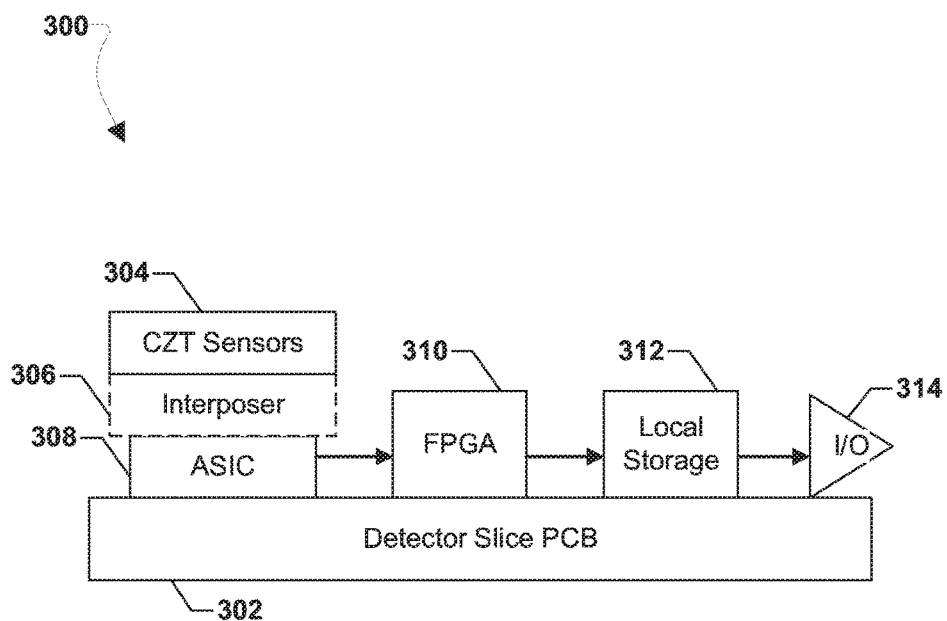
FIG. 3 is a functional block diagram of components in a detector element circuit of a radiation detector array according to various embodiments.

FIG. 3 is a functional block diagram of components in a detector element circuit 300 of a detector array, such as the detector 108 shown in FIG. 1, according to various embodiments. The detector element circuit 300 is mounted on a rotating part of the gantry 102. A detector array in a CT imaging system may have multiple detector element circuits 300. The components of the detector element circuit 300 may be placed on a common support, such as a detector element printed circuit board (PCB) 302, mounted on the moving (e.g., rotating or swinging) part of the gantry. The detector element circuit 300 may include a number of sensors 304, such as CZT pixel sensors or other types of X-ray radiation detectors. For example, in a multi-slice detector array, the sensors 304 may be arranged in a two dimensional array. The sensors 304 may be connected to an electronic component such as an ASIC 308 directly using a flip-chip technique or through an optional interposer 306. The ASIC 308 may be configured to receive, digitize, and bin the signals received from the sensors 304 in order to implement a photon counting detector. For example, the ASIC 308 may be configured to receive voltage signals corresponding to a photon that has hit one of the sensors 304, normalize the signal, remove noise from the signal, identify an energy bin for the photon based on the received voltage, and increment the count of the corresponding energy bin.

The ASIC 308 may transfer the photon count data to another electronic component such as a FPGA 310 which may perform additional signal processing on the photon count data. In alternative embodiments, the FPGA 310 may be an ASIC or any electronic component that may store and process the photon count data. The ASIC 308 transfers data to the FPGA 310 based on a certain clock rate, for example, the clock rate of the FPGA 310. The FPGA 310 may then transfer the bin count data to a local memory storage 312 according to the clock rate of the FPGA 310. The local memory storage 312 may be static random access memory (SRAM), dynamic RAM (DRAM), or any other type of volatile or non-volatile memory. The local memory storage 312 may physically comprise an integrated circuit chip which is mounted to the support individually or as part of the same chip as the FPGA and/or ASIC. The local memory storage 312 may provide a buffering function for the photon count data and may be clocked at a different clock rate than the FPGA 310. Thus the data in the local memory storage 312 may be read out and sent to an external computer via input/output (I/O) interface 314 at a rate that is independent of the output of the FPGA 310. The I/O interface 314 may include any wired or wireless communication interface, including Ethernet, universal serial bus (USB), fiber optics, WiFi, or co-axial cables.

Clocking the FPGA 310 and the local memory storage 312 at different clock rates may allow for control of the rate of output of the data from the detector element circuit 300 to the external computer. For example, the local memory storage 312 may be clocked at a slower speed than the FPGA 310. This means that the local memory storage 312 temporarily buffers the data from the FPGA 310 and outputs it at a rate that the I/O interface 314 and/or external computer may be able to handle. For example, the I/O interface 314 and/or applications on the external computer (e.g., imaging applications) may have certain bandwidth or data processing rate limitations and the local memory storage 312 may buffer the data to prevent bottlenecks or overloading of the I/O interface 314 and/or the applications. For example, a wired I/O interface 314 mounted on a rotating part of the gantry may have bandwidth or data processing rate limitations posed by the rotating slip ring connection between the rotating and non-rotating parts of the gantry. A wireless I/O interface 314 may comprise a wireless transceiver which has bandwidth or data processing rate limitations that are inherent in wireless communications devices and protocols.

Figure 4:
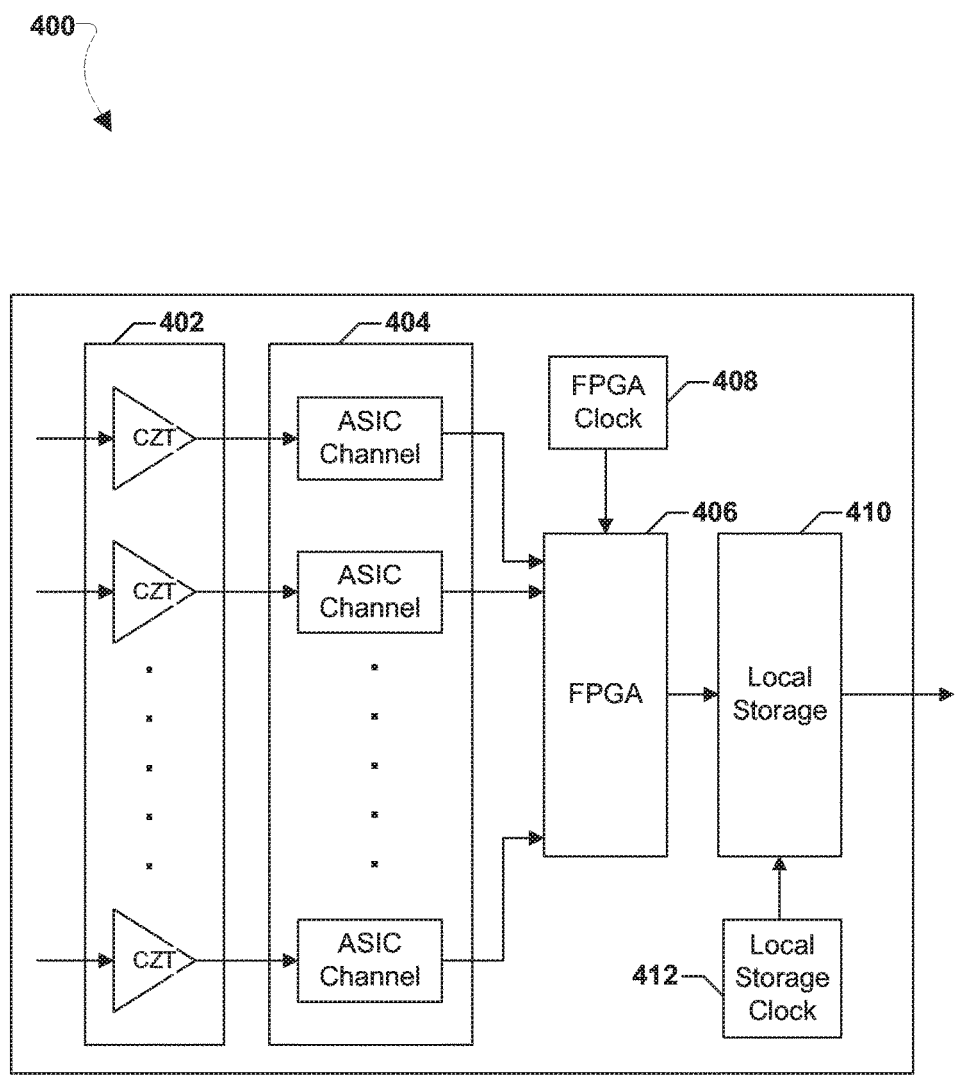
FIG. 4 is a circuit block diagram of components in a detector element circuit of a radiation detector array according to various embodiments.

FIG. 4 is a circuit block diagram of components in a detector element circuit 400 of a radiation detector array according to various embodiments. The circuit layout of the detector element circuit 400 may be an example configuration of the detector element circuit 300 illustrated in FIG. 3. A detector array in a CT imaging system may have multiple detector element circuits 400. The detector element circuit 400 may include a number of sensors 402, such as CZT pixel sensors or other types of X-ray radiation detectors. For example, in a multi-slice detector array, the sensors 402 may be arranged in a two dimensional array. Each sensor 402 may be connected to an electronic component such as an ASIC channel 404, which may be configured to receive, digitize, and bin the signals received from the sensors 402 to implement a photon counting detector. For example, the each ASIC channel 404 may receive voltage signals corresponding to a photon that has hit a corresponding sensor 402, normalize the voltage signal, remove noise from the signal, identify an energy bin for the photon based on the received voltage, and increment the count of the corresponding energy bin.

Each of the ASIC channels 404 may transfer the photon count data to another electronic component such as a FPGA 406 which may perform additional signal processing on the photon count data. The FPGA 406 may be clocked by a FPGA clock 408. That is, the rate at which the FPGA 406 inputs data from the ASIC channels 404 and outputs data may be controlled by the FPGA clock 408. The FPGA 406 may output the bin count data to a local memory storage 410. The local memory storage 410 may be SRAM, DRAM, or any other type of volatile or non-volatile memory. The local memory storage 410 may be clocked by a local storage clock 412, independent of the FPGA clock 410. That is, the rate at which the local memory storage 410 outputs data to an external computer may be controlled by the local storage clock 412.

The FPGA clock 408 and the local storage clock 412 may configured to clock the FPGA 406 and the local memory storage at different frequencies. The frequencies of the FPGA clock 408 and the local storage clock 412 may be hardwired, or may be set by a controller located on the gantry of the CT imaging system or an external computer. For example, an imaging or administrative application on the external computer may allow a user to set the clock rates of the FPGA clock 408 and/or the local storage clock 412 to control the relative output rates between the FGPA 408 and the local storage clock 412 of each detector element circuit 400 in the detector array. Thus the FPGA clock 408 and the local storage clock 412 may be used to control the buffering and output rates for data generated by a CT imaging system detector array in order to reduce bottlenecks or data transfer issues posed by a wired slip ring or wireless connection between the rotating part of the gantry and the computer.

Figure 5:
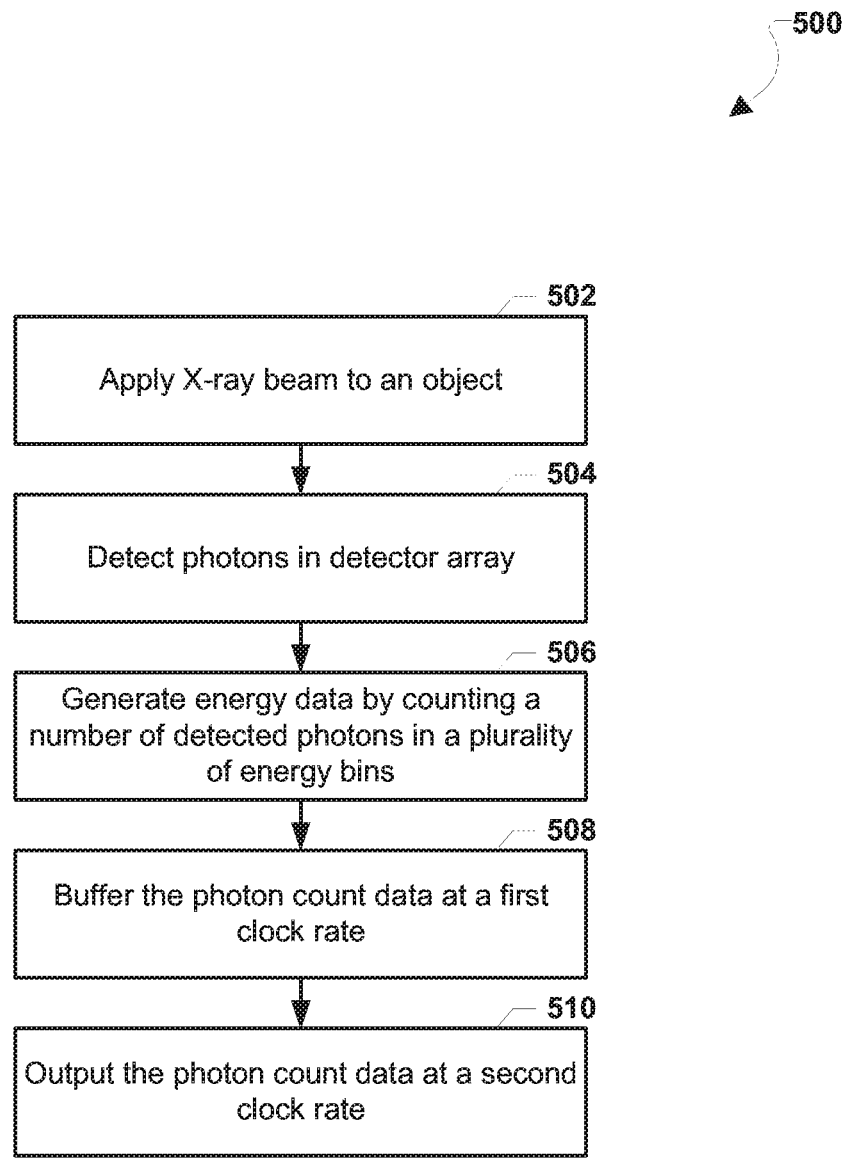
FIG. 5 is a process flow diagram of a method for operating a CT imaging system according to various embodiments.

FIG. 5 is a process flow diagram of a method 500 for operating a CT imaging system according to various embodiments. The method 500 may be performed by a CT imaging system (e.g., the CT imaging system 100) that includes an X-ray beam source and a detector array. The CT imaging system may be, for example, a helical CT scanner, a non-helical CT scanner, or a tomosynthesis CT scanner. The detector array may be a multi-slice detector array, in which each detector element includes a number of sensors (e.g., CZT pixel sensors) that are connected to a detector element circuit (e.g., the detector element circuit 400).

In block 502, the CT imaging system may apply an X-ray beam to an object in the CT imaging system. The object may be biological (e.g., a human patient) or non-biological. The CT imaging system may include an X-ray beam source that emits an X-ray beam through the object as the gantry upon which the X-ray beam source is located is rotated relative to the object.

In block 504, a detector element of the detector array on the opposite side of the gantry as the X-ray beam source may detect photons that have passed through and attenuated by the object. The detector array may be a multi-slice detector array with a number of detector elements. Each detector element may include a number of sensors (e.g., CZT pixel sensors), which may be arranged in a two-dimensional array. The detector element may detect the energy of photons emitted from the X-ray beam source that have passed through the object.

In block 506, the detector element may generate photon count data by counting the number detected photons in a plurality of energy bins using an electronic component that counts photons on the detector element, for example a photon counting ASIC (e.g., the ASIC channels 404). The ASIC may be configured to determine the energy of the detected photons and then sort the photons into energy bins based on their energy. Each energy bin may have an associated photon count. When a detected photon is sorted into a particular energy bin, the counter for that bin may be incremented. The number of energy bins may range from, for example, two to six.

In block 508, the detector element may buffer the photon count data at a first clock rate. For example, an electronic component such as a FPGA in the detector element may read the photon count data from the ASIC. The FPGA (e.g., the FPGA 406) may be controlled by a first clock (e.g., the FPGA clock 408) and be clocked at the first clock rate. Thus the FPGA may read the photon count data from the ASIC according to the first clock rate. The FPGA may also perform additional signal processing on the photon count data. The FPGA in the detector element may transfer the photon count data to a local memory storage in the detector element (e.g., the local memory storage 410) according to the first clock rate. The local memory storage may serve as a data buffer on the detector element before the data is output to an external computer (e.g., an imaging computer remote from the gantry). The local memory storage may be SRAM, DRAM, or any other type of volatile or non-volatile memory. The size of the local memory storage may be large enough to buffer data generated from the data collected by the detector element over one or more rotations of the gantry (e.g., on the order of Gb).

In block 510, the detector element may output the photon count data at a second clock rate. For example, the local memory storage may be controlled by a second clock (e.g., the local memory storage clock 412) and be clocked at the second clock rate. The second clock rate may be different from the first clock rate. In other words, the clock rates of the FPGA and the local memory storage may be independently controlled such that the local memory storage may output the photon count data at a different rate than the FPGA reads the photon count data. The second clock rate may be selected such that the data output rate reduces bottlenecks and other issues in other parts of the CT imaging system, such as an external computer than receives the data and generates images, and/or a wired or wireless interface that connects the detector element to the external computer. For example, the second clock rate may be selected to be slower than the first clock rate as to limit the data output rate if the bandwidth of the communications interface, external computer hardware, or an imaging application on the external computer is limited. In this manner, the method 500 allows the detector elements of a detector array to output data at time intervals that are convenient from the system point of view.

While the disclosure has been described in terms of specific embodiments, it is evident in view of the foregoing description that numerous alternatives, modifications and variations will be apparent to those skilled in the art. Each of the embodiments described herein can be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

The invention claimed is:

1. A detector element circuit in a CT imaging system, comprising:
   a plurality of radiation sensors for detecting photons attenuated by an object;
   a first electronic component configured to determine an energy of photons detected by the plurality of radiation sensors and generate digitized photon count data, wherein the digitized photon count data comprises a digitized count of detected photons in one or more energy bins;
   a field programmable gate array (FPGA) configured to receive the digitized photon count data from the first electronic component and generate an output representing the digitized photon count data, wherein the FPGA comprises a FPGA clock configured to control a rate at which the FPGA receives the digitized photon count data from channels of the first electronic component and at which the FPGA outputs the output representing the digitized photon count data; and
   a local memory storage configured to receive the output representing the digitized photon count data from the FPGA and comprising a local storage clock configured to control a rate at which the local memory storage generates buffered output data derived from the digitized photon count data,
   wherein:
   the FPGA clock and the local storage clock are set such that the FPGA is clocked at a first clock rate and the local storage element outputs the buffered output data at a second clock rate; and
   the second clock rate and the first clock rate are selected to reduce bottlenecks or data transfer issues imposed by bandwidth limitations between the local memory storage and a computer of the CT imaging system that is configured to receive the buffered output data from the local memory storage.

2. The detector element circuit of claim 1, wherein the local memory storage is further configured to output the digitized photon count data to an input/output interface at the second clock rate.

3. The detector element circuit of claim 1, wherein the plurality of radiation sensors comprises a plurality of CZT sensors.

4. The detector element circuit of claim 1, wherein the second clock rate is slower than the first clock rate.

5. The detector element circuit of claim 1, wherein the first electronic component is an ASIC.

6. The detector element circuit of claim 1, wherein the local memory storage buffers the digitized photon count data received from the FPGA.

7. The detector element circuit of claim 1, wherein the first electronic component is an ASIC, the electronic component is a FPGA, and the plurality of radiation sensors, the ASIC, the FPGA and the local memory storage are mounted on a common support.

8. A CT imaging system, comprising:
   a gantry;
   a radiation source mounted to the gantry; and
   a detector array mounted to the gantry,
   wherein:
   the detector array is configured to detect radiation emitted from the radiation source and attenuated by an object located in the gantry;
   the detector array comprises a plurality of instances of the detector element circuit of claim 1; and
   the computer is located remotely from the gantry and is configured to receive data buffered by the local memory storage of each detector element circuit.

9. The CT imaging system of claim 8, wherein the local memory storage in each of the plurality of detector element circuits is clocked at a separate clock rate than other components in the detector element circuit.

10. The CT imaging system of claim 8, wherein a moving part of the gantry is configured to make a plurality of circular paths relative to the object.

11. The CT imaging system of claim 8, wherein the radiation sensors and the local memory storage are mounted on a common support, and the common support is mounted to a rotating part of the gantry.

12. A method of operating a CT imaging system, comprising:
   detecting photons emitted by an X-ray source and attenuated by an object;
   generating digitized photon count data by counting a number of detected photons in a plurality of energy bins;
   buffering the digitized photon count data at the first clock rate employing the detector element circuit of claim 1; and
   outputting the digitized photon count data at the second clock rate from the detector element circuit.

13. The method of claim 12, wherein a detector array in the CT imaging system detects the photons, and wherein the detector array comprises a plurality of detector element circuits that each include a plurality of radiation sensors.

14. The method of claim 13, wherein each detector element circuit includes a local memory storage for buffering the digitized photon count data, and each detector element circuit is located on a rotating part of a gantry of the CT imaging system.

15. The method of claim 14, wherein the local memory storage is clocked at the second clock rate.

16. The method of claim 14, wherein each detector element circuit includes an electronic component for transferring the digitized photon count data to the local memory storage at the first clock rate.

* * * * *